United States Patent [19]

Kalk et al.

[11] Patent Number: 4,481,375

[45] Date of Patent: Nov. 6, 1984

[54] BINUCLEAR RHODIUM COMPLEX AS A HYDROFORMYLATION AND HYDROGENATION CATALYST

[75] Inventors: Philippe Kalk, Castanet; René Poilblanc, Castanet Colosan; Antoine Gaset, Toulouse, all of France

[73] Assignee: Produits Chimiques Ugine Kuhlmann, Courbevoie, France

[21] Appl. No.: 94,795

[22] Filed: Nov. 16, 1979

Related U.S. Application Data

[62] Division of Ser. No. 960,001, Nov. 13, 1978, Pat. No. 4,215,066.

[30] Foreign Application Priority Data

Nov. 10, 1977 [FR] France ................................ 7733865

[51] Int. Cl.³ ...................... C07C 45/49; C07C 45/50
[52] U.S. Cl. .................... 568/454; 568/882; 568/883; 260/429 R; 502/159; 502/166
[58] Field of Search ............... 568/454, 909, 882, 883; 252/431 P; 260/429 R

[56] References Cited

U.S. PATENT DOCUMENTS 3,501,531  5/1970  Wilkinson ........................... 568/454
3,794,671  2/1974  Wilkinson ........................... 568/454
3,933,919  1/1976  Wilkinson ........................... 568/454
3,954,877  5/1976  Gipson ................................ 568/454

Primary Examiner—Werren B. Lone
Attorney, Agent, or Firm—Sigalos & Levine

[57] ABSTRACT

The present invention relates to hydrogenation and hydroformylation catalysts based on a binuclear rhodium complex having the formula:

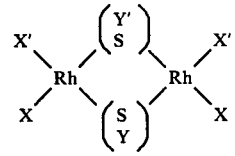

wherein X and X' can be the same or different; when X and X' are the same they are organic tertiary phosphite groups and when different X is a CO group and X' is an organic tertiary phosphite group or an aromatic phosphine group, and SY and SY' are thiolato groups. The invention also comprises the processes of hydroformylation and hydrogenation using such catalytic complex.

7 Claims, No Drawings

BINUCLEAR RHODIUM COMPLEX AS A HYDROFORMYLATION AND HYDROGENATION CATALYST

This is a division of application Ser. No. 960,001, filed Nov. 13, 1978, now U.S. Pat. No. 4,215,066.

BACKGROUND OF THE INVENTION

Hydroformylation catalysts based on a binuclear rhodium complex are known, more particularly catalytic species of the type:

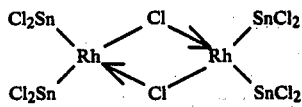

are described in the U.S. Pat. No. 3,501,531.

Such catalysts, although giving good results, present the disadvantage of being comparatively inactive which necessitates extremely long reaction times or the use of high concentrations of catalyst which have the disadvantage of being costly. On the other hand, the application of high temperatures, which might reduce the reaction times, leads to a loss in the selectivity for obtaining the aldehyde due to the hydrogenation of the aldehydes into alcohols.

SUMMARY OF THE INVENTION

The novel catalysts of the present invention make it possible to perform hydroformylation reactions at moderate temperatures and pressures with a very high selectivity for the formation of aldehyde and they have also been found to be excellent hydrogenation catalysts.

Briefly stated, the catalysts of the present invention have the formula:

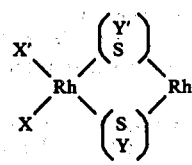

wherein X and X' can be the same or different; when X and X' are the same they are organic tertiary phosphite groups, and when different X is a CO group and X' is an organic tertiary phosphite or an aromatic phosphine group, and SY and SY' are thiolato groups. The invention also comprises the processes of hydroformylation and hydrogenation utilizing such catalysts, as hereinafter described.

DETAILED DESCRIPTION

In the catalyst, the two radicals Y and Y', whether the same or different, are not critical since they are inert with respect to the reagents or the reactants of the hydroformylation or hydrogenation reaction, and to the catalyst itself. They are customarily saturated aliphatic, arylalkyl or alkylaryl radicals. Y and Y' are generally chosen as a function of the way in which the catalyst is used in the hydroformylation or hydrogenation process. Indeed, one of the advantages of the catalytic system which is the object of the invention is to be capable of use in both homogeneous catalysis and in supported homogeneous catalysis.

Thus, for example, if it is desired to operate in homogeneous catalysis, in which case the catalyst must be dissolved in the reactive medium, it is desirable to choose for Y and Y' radicals those having from 1 to 6 carbon atoms; preferred being the methyl, ethyl, propyl, isopropyl, butyl, isobutyl, tertiobutyl, pentyl, neopentyl, phenyl radicals. The tertiobutyl group in particular has been found to be highly satisfactory.

If, on the other hand, it is desired to operate in supported homogeneous catalysis, then the catalyst is fixed on an inert substrate (of the type commonly used in making supported catalysts) under the conditions of the hydroformylation or hydrogenation. In this case, at least one of the Y or Y' radicals may represent the residue (moiety) of a polymeric chain having contained a thiol function. The polymeric chains with thiol function are known per se; they are obtained, for example, by treating chlorinated polymers such as polyvinyl chloride, polychloroethylene, polychloroprene or again a chloromethylated polystyrenic resin, with thiourea.

The phosphite and phosphine groups which occur in the composition of this catalyst are known and correspond to those customarily used in catalysts based on a monoclear rhodium complex, as in the case, for example, in British Pat. No. 1,138,601.

Generally speaking, the phosphites most currently used are straight-chain or branched alkyl phosphites containing from 1 to 20 carbon atoms. Branched-chain alkyl phosphites are also understood to mean the products in which the alkyl group originates from the mixture of oxo alcohols obtained from trimers of propylene. Likewise, customarily suitable are the aryl, alkylaryl or arylalkyl phosphites such as the phenyl, xylyl, tolyl, octylphenyl, nonylphenyl, dodecylphenyl, and benzyl phosphites.

Among the aromatic phosphines used, the most current is triphenyl phosphine which has the advantage of being readily available. However, heavier aromatic phosphines, such as the trialkylaryl phosphines, e.g., tritolyl, trinonylphenylphosphine or others, may also be advantageously used if, for reasons of boiling point, it is necessary to use heavy phosphines in the process.

These catalysts, the object of the invention, may conveniently be prepared from binuclear rhodium complexes with a μ-chloro bridge, e.g., di-μ-chlorotetracarbonyl dirhodium (I), a method of preparation of which is indicated in *Inorganic Syntheses*, Vol. 8 (1966) pp. 211, or again di-μ-chlorotetraethylene dirhodium (I), a method of preparation of which is indicated in the *Inorganic Chemistry* Revue, Vol. 1 (1962) pp. 722. In another mode of preparation of these catalysts, di-μ-chlorobis (ηcyclooctadiene 1-5)-dirhodium (I), the preparation of which from RhCl$_3$.3H$_2$O is described in the *Journal of Chemical Society*, 1957 pp. 4735. For the preparation of the catalysts containing CO groups, it may be advantageous to use di-μ-chloro diethylene dicarbonyl dirhodium, a method of preparing which is described in the *Journal of Chemical Society*, Section A of 1968 pp. 211.

Starting from one of the complexes enumerated hereinbefore, the catalyst of desired structure is obtained by methods known per se, of ligand substitutions performed in an appropriate solvent, e.g., toluene or methylene chloride. The following reactions illustrate the possibilities of syntheses which one skilled in this art can readily adapt according to the catalyst complex desired:

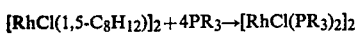

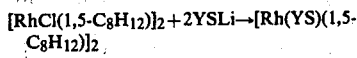

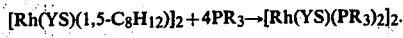

Likewise, catalytic complexes containing carbon monoxide may be prepared by performing the following reactions in a suitable solvent, e.g., toluene or methylene chloride:

In the above reactions, $PR_3$ denotes the phosphine or phosphite which it is required to integrate into the molecule and YSLi is a lithium thiolate.

Generally speaking, the reactions enumerated hereinbefore are performed easily by simply mixing the reagents, which are used in the stoichiometric proportions of the reaction, at moderate temperatures, e.g., between ambient temperature and 70° C.

In case the catalyst is fixed on an inert substrate (support), the same type of reaction as those previously described is used for its preparation. For example, starting from a solid substrate upon which —SH functional groups have previously been grafted by any appropriate conventional method, the reaction can be represented schematically in the following manner:

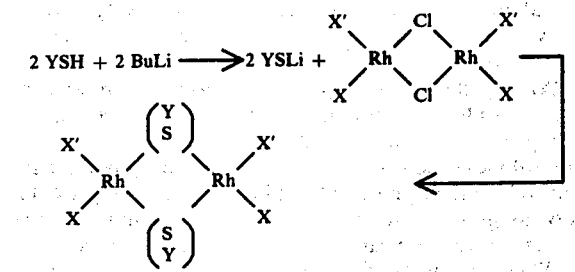

In the foregoing reaction, Y is a residue (moiety) of a polymeric chain, BuLi is butyllithium, and X and X', identical or different, are as previously defined. In the case where X' is a phosphine and X the CO group, this method makes it possible to graft the binuclear rhodium catalyst complex onto a suitable substrate.

The contrary method, which would consist in first of all reacting $[RhCl(CO)_2]_2$ with YSLi, leads ultimately, when two of the CO are replaced by a phosphine, to the destruction of the grafted binuclear catalyst complex.

In one of its aspects, the present invention relates to a hydroformylation of olefins into aldehydes, which consists in reacting said olefins with a mixture of hydrogen and carbon monoxide, and which is characterized by the use, as catalyst, of the binuclear rhodium catalyst complexes previously described.

The process may be performed in homogeneous phase, the catalyst being dissolved in the reagents, continuously or discontinuously, with or without solvent. The use of a solvent, other than the olefin itself, may be advantageous where the olefin is gaseous or where the solubility of the catalyst complex under the conditions of the reaction is weak. Any type of solvent may be used which is inert under the conditions of the reaction, such as e.g., aromatic hydrocarbons such as benzene, toluene, xylene, and ethylbenzene.

The process may also be performed in heterogeneous phase, when the catalyst may, for example, be in dispersed form in the reactive media or as a fixed bed, where in the complexes previously described, at least one of the Y radicals connotes the residues of a polymeric chain.

The reaction temperature may be between approximately 20° C. and approximately 250° C. with the adoption of higher temperatures presenting no additional advantages. In practice, the temperature will preferably be within the range from 20° C. to 150° C. The total pressure of hydrogen and carbon monoxide may vary within fairly wide limits. However, one of the advantages of the process is to be able to use low pressures. Thus, although total pressures of hydrogen and carbon monoxide above 100 bars can be used, it will be more advantageous to use pressures of between 1 and 50 bars, preferably between 1 and 25 bars. The molar ratio $H_2/CO$ may also vary within fairly wide limits, for example, between 1/10 and 10/1, preferably between 1/5 and 5/1, and more particularly, between 1/2 and 4/1.

The quantities of catalysts to be used are not especially critical; they depend to a large degree upon the various reaction parameters adopted and upon the desired reaction time. Thus, these concentrations may vary in a range of between $10^{-6}$ and $10^{-2}$ moles of catalyst per mole of olefin to be hydroformylated. Generally, quantities of catalyst of between $10^{-5}$ and $10^{-3}$ moles of catalyst per mole of olefin make it possible to perform the hydroformylation reaction under the conditions previously described and with the desired conversion rate, in times of between approximately 1 hour and approximately 20 hours.

The catalysts according to the invention are customarily used alone. However, in some cases it may be worthwhile to associate them with an excess of phosphite (P). This excess may vary in fairly wide proportions, the P/Rh ratio may be within the range from 1/1 to 10/1.

These catalysts can easily be separated from the reactive media by any appropriate and known fractionation method. They are generally more stable than the majority of the known catalysts of the prior art and it is possible, for example, to distill the reaction products and recycle the catalytic system contained in the distillation dregs to another operation. The distillation may be performed at normal pressure or at reduced pressure, preferably in the presence of an inert gas such as nitrogen, argon, or synthetic gas: $CO + H_2$. It is also possible, in the case of solid catalyst, to separate by decantation, filtration, or quite simply by leaving it in place in a continuous reactor. The hydroformylation in the presence of the catalysts claimed presents the advantage of leading to the aldehydes with very high selectivity; that is to say, the yields in aldehydes counted with reference to the olefin converted are practically quantitative.

In another of its aspects, the present invention concerns the use of the binuclear rhodium complexes previously described as hydrogenation catalysts. These catalysts permit the hydrogenation of unsaturated organic bonds (organic compounds with at least one unsaturated bond), under mild conditions; that is to say, at weak hydrogen pressure and at low temperatures. They are particularly appropriate in the case of the hydrogenation of the aliphatic or aromatic olefins or of any other aromatic or nitrogenated aromatic compound.

The hydrogenation process employing the binuclear rhodium catalyst complexes which are the objects of the invention, may be performed in homogeneous phase and in continuous or discontinuous process, with or without solvent. The use of a solvent may be advantageous where the product to be hydrogenated is solid or where the solubility of the complex, under the conditions of the hydrogenation, is weak. Any type of solvent may be used, more particularly, solvents containing no unsaturation, such as the alkanes, the cycloalkanes, the alcohols, the ethers, the chlorinated alkanes, and the like, or again, solvents inert under the conditions chosen to perform a given hydrogenation reaction, such as, for example, aromatic hydrocarbons which are more difficult to hydrogenate than the olefins.

The hydrogenation process may also be performed in heterogeneous phase where, in the catalysts described, at least one of the Y radicals denotes the residue of a polymeric chain.

As already stated, one of the advantages of the process according to the invention lies in the fact that it does not necessitate the application of very high temperatures. Although temperatures of 150° C. or more may be used, in practice, temperatures within the range from around 20° C. to 120° C. are suitable. The increase in the reaction temperature has the effect of increasing the kinetics of hydrogenation. However, for the choice of the adequate temperature, it is worthwhile taking into account the selectivity of the hydrogenation when this is desired. For example, in the majority of cases it is possible to hydrogenate the nitro function of an aromatic compound without hydrogenating the aromatic radical by operating at temperatures of between approximately 20° C. and approximately 70° C. according to the catalyst chosen, whereas the adoption of higher temperatures, of the order of 100° C., permits the molecule to be totally hydrogenated.

The hydrogen pressure is not critical. Although it is possible to adopt pressures of between 1 and 200 bars or more, pressures of between 1 and 50 bars, preferably between 1 and 25 bars, are sufficient.

The quantities of catalysts to be used depend upon the various reaction parameters adopted and, as has already been stated, upon the desired reaction time. Generally speaking, quantities of catalyst of between $10^{-6}$ and $10^{-2}$, preferably between $10^{-5}$ and $10^{-3}$ moles of catalyst per function (unsaturation) to be hydrogenated are suitable and lead to reaction times generally within the range between approximately 1 hour and approximately 20 hours, under the conditions of temperature and hydrogen pressure previously described.

The catalysts are customarily used alone in hydrogenation. However, in certain cases it may be advantageous to associate them with an excess of phosphite (P). This excess may vary in such a way that the P/Rh ratio is within the range between 1/1 and 10/1 and preferably between 1/1 and 2/1.

These catalysts can easily be separated from the reactive medium by any appropriate fractionation method. It is, for example, possible to distill the reaction products and recycle the catalytic system contained in the distillation dregs to another operation. The distillation may be performed under normal pressure or under reduced pressure, preferably in the presence of an inert gas such as nitrogen or argon or hydrogen. It is also possible, in the case of a solid catalyst, to separate it from the reactive medium by decantation or filtration, or quite simply leave it in place in a continuous reactor.

The following examples are given to illustrate the best modes for carrying out the present invention, but are not to be construed as limiting the scope thereof.

EXAMPLE 1

Into a 1.5 liter stainless steel reactor, equipped with a stirring system, a temperature probe, a pressure gauge, and capable of withstanding a pressure of 300 bars, there is introduced a mixture of 200 g. of hexene-1, 200 g. of toluene and 0.684 g. of di-μ-tertiobutylthiolato tetrakis (trimethylphosphite) dirhodium (I). The installation is carefully purged with synthetic gas of molar ratio of $H_2/CO=1/1$.

A pressure of 20 bars of this same synthetic gas is then established and the temperature is increased progressively up to 48° C., at which temperature a pressure drop indicates the beginning of the reaction. The pressure in the autoclave is then maintained by adding known volumes of synthetic gas of molar ratio $H_2/CO=1/1$ and the temperature is raised progressively up to 115° C. so as to maintain an approximately constant gas consumption, of the order of 1 liter per minute. At the end of 2 hours, 105 liters of synthetic gas have been consumed. After returning to ambient temperature and releasing the gas contained in the autoclave, 457 g. of a mixture is recovered which is distilled under a reduced nitrogen pressure of 200 mm Hg. 443.5 g. of distillate is recovered which contains 243 g. of heptanals, of which 65.2% is n-heptanal. Chemical analysis and examination by vapour phase chromatography reveal no trace of alcohols or of $C_7$ formiates.

The distillation residue, containing the catalytic system, represents 1.25 g. of product.

EXAMPLE 2

The distillation residue, containing the catalyst, obtained in Example 1, is dissolved in 200 g. of toluene, and the hydroformylation of 200 g. of hexene-1 is repeated under the same conditions as previously. The reaction is performed between 58° C. and 110° C., and at the end of 130 minutes 103.5 liters of synthetic gas of molar composition $H_2/CO=1$ have been consumed. After distillation 444.2 g. of distillate is recovered which contains 244.8 g. of heptanals of which 63.3% is n-heptanal. As previously, no trace of alcohols or of $C_7$ formiates is detected.

The residue of the distillation, containing the catalytic system, represents 5.9 g. of product.

EXAMPLE 3

The distillation residue of Example 2 is taken in 200 g. of toluene and the hydroformylation of a fresh charge of 200 g. of hexene-1 is repeated under the same conditions as in Example 1, except for the fact that 0.41 g. of trimethyl phosphite is added in excess, so as to attain a molar ratio P/Rh=4. The reaction is performed between 68° and 104° C., and at the end of 100 minutes 103.4 liters of synthetic gas have been consumed. After distillation, 453.1 g. of distillate is recovered which contains 246.7 g. of heptanals of which 72.3% is n-heptanal. As previously, no trace of alcohols or of $C_7$ formiates is detected.

The residue of the distillation, containing the catalytic system, represents 7.35 g. of product.

EXAMPLE 4

The hydroformylation of 200 g. of hexene is repeated with a fresh charge of catalyst, under the same conditions as in Example 1, except for the fact that the initial pressure of 20 bars is established with a synthetic gas of molar ratio $H_2/CO=2$. The reaction is performed between 56° C. and 123° C., and at the end of 165 minutes, 93.4 liters of synthetic gas of molar ratio $H_2/CO=1$ have been consumed. After distilling the reaction products, 437.4 g. of distillate is recovered which contains 235.1 g. of heptanals, of which 62.3% is n-heptanal. Still no trace of formiates is detected, and only traces of heptanols which represent approximately 0.2% by weight of the aldehydes obtained.

The residue of the distillation, containing the catalytic system, represents 3.85 g. of product.

EXAMPLE 5

Into a 56.5 cm$^3$ stainless steel reactor equipped with a magnetic agitator, with a temperature probe and with a pressure regulator, 15 ml. of benzene and 0.9 mg. of di-μ-ethylthiolato dicarbonyl bis (triphenylphosphine) dirhodium (I) of formula $[Rh(SC_2H_5)CO\ P\phi_3]_2$ are introduced, and the autoclave is purged with synthetic gas of molar ratio $H_2/CO=1/1$.

A pressure of 15 bars is then established with a mixture of gas of molar ratio propylene/$H_2$/CO of approximately 1/1/1 and the temperature is increased progressively up to 60° C., at which temperature a pressure drop indicates the beginning of the reaction. The pressure in the autoclave is then maintained by the addition of known volumes of the propylene/$H_2$/CO mixture already mentioned and the temperature is gradually increased up to 85° C., so as to maintain a consumption of gas of the order of 0.1 liters per period of 5 minutes. After 9 hours, 11 liters of gas have been consumed, which represents a consumption of approximately 6.4 g. of propylene. After returning to ambient temperature and releasing the gas contained in the autoclave, analysis by vapor phase chromatography shows that 9.3 g. of butyraldehydes have been obtained in a straight-chain/branched ratio equal to 6.1/1. On the other hand, no trace of products other than the initial benzene and the butyraldehydes is detected.

EXAMPLE 6

Into the reactor of Example 5, there is introduced 15 ml. of a $C_{12}$-$C_{14}$ olefin cut consisting of α-olefins, 15.7 mg. of di-μ-tertiobutyl-thiolato tetrakis (trilauryl phosphite) dirhodium (I) of formula $[Rh(StBu)(P(OC_{12}H_{25})_3)_2]_2$ and the autoclave is purged with synthetic gas of molar ratio $H_2/CO=2/1$.

A pressure of 50 bars of this same synthetic gas is then established and the temperature is increased up to 68° C., at which temperature a pressure drop indicates the start of the reaction. The pressure is then maintained at 50 bars by the addition of known volumes of a synthetic gas of composition $H_2/CO=1/1$ and the temperature is increased progressively up to 145° C. so as to maintain a consumption of approximately 0.2 liter per period of 10 minutes. After 2.5 hours, 2.56 liters of synthetic gas have been consumed. After returning to ambient temperature and relaxing the gas contained in the autoclave, 12.86 g. of a mixture is recovered, chromatographic analysis of which reveals that it is composed of 76.1% of $C_{13}$-$C_{15}$ aldehydes in a straight-chain/branched ratio equal to 2.1/1. No trace of formiates is found, and only 0.4% of the aldehydes have been hydrogenated into alcohols.

EXAMPLE 7

Into the reactor of Example 5, there is introduced 20 cm$^3$ of hexene-1 and 12 mg. of di-μ-tertiobutylthiolato-tetrakis (trimethyl-phosphite) dirhodium of formula $[Rh(StBu)(P(OCH_3)_3)_2]_2$.

After closing the reactor and purging by a current of hydrogen, a hydrogen pressure of 25 bars is established and the temperature is raised up to 100° C., maintaining the hydrogen pressure at 25 bars. After 1 hr. 30 min., examination of the reaction products by vapor phase chromatography shows that the hydrogenation of the hexene-1 is quantitative.

EXAMPLE 8

Into a 500 ml. glass reactor, equipped with an agitation system, with a supply of gas at constant pressure, with a heating system and with a temperature probe, there are introduced successively 10 ml. of hexene-1, 10 ml. of benzene and 193.6 mg. of di-μ-tertiobutylthiolato tetrakis (trimethylphosphite) dirhodium. After having purged the autoclave with a synthetic gas, of molar composition $H_2/CO=1$, a pressure of 5 bars of the same gas is established.

After starting the agitation, the temperature is raised to 80° C., and after 8 hours reaction, 8.8 g. of heptanals are obtained in a straight-chain/branched ratio equal to 5.6/1. Examination by vapor phase chromatography reveals no trace of products other than the initial products and the heptanals.

EXAMPLE 9

A resin containing R-S-H functional groups was obtained from a chloromethylated polystyrenic resin by a known method; by treating the chloromethylated resin with thiourea, and presents the following approximate analysis in percent by weight;
C: 75.97%—H: 6.80%—Cl: 0%—S: 13.53%.

After washing with 20 ml. of tetrahydrofuran (THF), 327 mg. of this resin are placed in suspension in 10 ml. of THF and treated with 3.023 moles of butyllithium dissolved in 30 ml. of THF with reflux for 20 hours. After washing the resin in THF, 531 mg. of di-μ-chlorotetrakis (trimethylphosphite) dirhodium (I) $[RhCl(P(OCH_3)_3)_2]_2$, dissolved in 40 ml. of THF, are added. After 45 hours heating with reflux, elimination of the supernatant solution, washing in THF, and drying in vacuo, a supported catalyst is obtained having the following approximate analysis in percent by weight:
C: 67.48%—H: 6.34%—S: 11.18%—P: 2.50%—Rh: 4.16%.

Into the reactor of Example 8, 189 mg. of this catalyst, 10 ml. of hexene-1, and 10 ml. of benzene are introduced. After closing the reactor, it is purged with synthetic gas of molar composition $H_2/CO=2$, and a pressure of 4.5 bars of this same synthetic gas is established. After 24 hours reaction at 20° C., 3.1 g. of heptanals in a straight-chain/branched ratio equal to 6/1 are obtained.

EXAMPLE 10

122 mg of the supported catalyst of Example 9 and 10 ml. of nitrobenzene are placed in the same reactor. After having purged the reactor with hydrogen, a hydrogen pressure of 5 bars is established, then the temperature is raised up to 50° C. After 48 hours reaction time, hydrogenation of the nitrobenzene is quantitative and analysis by vapor phase chromatography shows that 89% has been converted into aniline, and 11% into cyclohexylamine.

EXAMPLE 11

The previous hydrogenation experiment of Example 10 is repeated with 10 ml. of aniline, this time raising the temperature to 90° C. After 6 hours, it is found that 30% of the aniline has been converted into cyclohexylamine.

EXAMPLE 12

A supported catalyst is prepared by the same method as that used in Example 9, except for the fact that $[RhCl(P(OCH_3)_2)_2]_2$ is replaced by di-$\mu$-chloro dicarbonyl bis (trimethylphosphite) dirhodium (I) of formula $[RhCl(CO)(P(OCH_3)_3)]_2$. The catalyst obtained, when examined by infrared spectroscopy in dispersion in CsBr, exhibits a carbonyl band at 1990 cm$^{-1}$, comparable with the band observed at 1992 cm$^{-1}$ on the derivative $[Rh(S-\phi)(CO)P(OCH_3)_3]_2$, quite distinct from the band at 2005 cm$^{-1}$ observed with the initial $\mu$-chloro complex.

Into the reactor of Example 8, 64 mg. of this supported catalyst, 10 ml. of benzene, 10 ml. of hexene-1 are charged and, after closing and purging the apparatus, a hydrogen pressure of 5.6 bars is established. After 8 hours reaction at 20° C., 5.58 g. of hexane are obtained, representing a yield in the hydrogenation of hexene-1 of approximately 80%. Analysis by vapor phase chromatography reveals no trace of cyclohexane.

EXAMPLE 13

265.4 mg of di-$\mu$-tertiobutylthiolato tetrakis (trimethylphosphite) dirhodium (I), 10 ml. of hexene-1, and 10 ml. of benzene are charged into a glass reactor identical to that used previously. After closing the reactor, it is purged by a current of hydrogen, and a hydrogen pressure of 1 bar is established. The solution then changes from the initial yellow color to red. The temperature of the reactor is maintained at 25° C. by a circulation thermostat. After 60 minutes, analysis of the reaction products by vapor phase chromatography reveals that 95% of the hexene-1 has been hydrogenated to hexane.

EXAMPLES 14 to 24

Complexes of different structures were tested according to the method of Example 13, as hydrogenation catalysts on several types of products.

The results obtained are set forth in Table I below.

TABLE I

| Ex. | Catalyst Complex | Product to be hydrogenated and, where used, solvent | Con. of catalyst moles of cat. moles of prod. | Temps. °C. | Hydrogen pressure | Time min. | Yields of hydrogenated products based on initial products; in % |
|---|---|---|---|---|---|---|---|
| 14 | $[Rh(St.Bu)(P(OCH_3)_3)_2]_2$ | 20 ml. hexene-1 | 2.8 $10^{-4}$ | 35° | 1 | 420 | 29 hexane |
| 15 | $[Rh(St.Bu)(P(OCH_3)_3)_2]_2$ | 10 ml. cyclohexene 10 ml. benzene | 1.5 $10^{-4}$ | 40° | 3 | 90 | 59 cyclohexane |
| 16 | $[Rh(St.Bu)(P(OCH_3)_3)_2]_2$ | 10 ml. nitrobenzene 10 ml. benzene | 1.4 $10^{-4}$ | 55° | 3 | 1,020 | 14.3 aniline |
| 17 | *$[Rh(St.Bu)(P(OC_{12}H_{25})_3)_2]_2$ | 10 ml. cyclohexene 10 ml. benzene | 1.2 $10^{-4}$ | 40° | 3 | 90 | 52 cyclohexane |
| 18 | **$[Rh(St.Bu)(P(OC_{10}H_{21})_3)_2]_2$ | 10 ml. cyclohexene 10 ml. benzene | 1.3 $10^{-4}$ | 40° | 3 | 90 | 53 cyclohexane |
| 19 | $Rh(SC_2H_5)(P(OCH_3)_3)_2]_2$ | 10 ml. cyclohexene 10 ml. benzene | 5 $10^{-5}$ | 40° | 3.5 | 450 | 2 cyclohexane |
| 20 | (see structure below) | 10 ml. cyclohexene 10 ml. benzene | 8 $10^{-5}$ | 40° | 3 | 320 | 35 cyclohexane |
| 21 | $[Rh(St.Bu)(P(O\phi)_3)_2]_2$ | 20 ml. hexene-1 80 ml. benzene | 4 $10^{-4}$ | 40° | 5 | 120 | 100 hexane |
| 22 | $[Rh(St.Bu)(CO)(P\phi(CH_3)_2)]_2$ | 10 ml. cyclohexene 10 ml. benzene | 1.8 $10^{-4}$ | 40° | 3 | 900 | 55 cyclohexane |
| 23 | $[Rh(St.Bu)(CO)(P(OCH_3)_3)]_2$ | 10 ml. hexene-1 10 ml. benzene | 1.3 $10^{-4}$ | 30° | 3 | 480 | 40 hexane |
| 24 | $[Rh(S\phi)(P(OCH_3)_3)_2]_2$ | 10 ml. hexene-1 10 ml. benzene | 9 $10^{-5}$ | 40° | 3 | 420 | 30 hexane |

Structure for Example 20:

$$(CH_3O)_3P\diagdown_{Rh}\diagup^{S}\diagdown_{Rh}\diagup P(OCH_3)_3$$
$$(CH_3O)_3P\diagup\quad\diagdown^{S}\diagdown P(OCH_3)_3$$
$$\quad\quad\quad\quad C_2H_5 \text{ (top)};\ terC_4H_9\text{ (bottom)}$$

*tri-n-dodecyl phosphite
**tri-isodecyl phosphite derived from an industrial $C_{10}$ OXO-alcohol produced from trimers of propylene.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. In the process for the hydroformylation of olefins or in the process for the hydrogenation of organic compounds having at least one unsaturated bond, the improvement comprising carrying out the reaction in the presence of a catalyst having the formula:

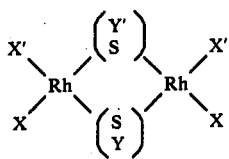

wherein X and X' can be the same or different; when X and X' are the same, they are organic tertiary phosphite groups and when different, X is a CO group and X' is an organic tertiary phosphite group or an aromatic phosphine group, and SY and SY' are thiolato groups, there being present from about $10^{-6}$ to $10^{-2}$ moles of said catalyst per mole of olefin to be hydroformylated or per unsaturated bond to be hydrogenated.

2. The process of claim 1 wherein the Y and Y' radicals can be the same or different and are selected from saturated aliphatic, aralkyl, or alkylaryl radicals.

3. The process of claim 2 wherein Y and Y' are selected from radicals containing 1 to 6 carbon atoms.

4. The process of claims 2 or 3 wherein at least one of Y or Y' is the moiety of a polymer with a thiol function.

5. The process of claim 4 wherein the polymer is a polystyrenic resin.

6. The process of claims 1, 2, or 3 wherein the catalyst has a phosphite to rhodium ratio between about 1/1 to 10/1.

7. The process of claim 1 wherein the improvement is in the reaction for the hydroformylation of olefins.

* * * * *